US010287619B2

(12) United States Patent
Iwamoto et al.

(10) Patent No.: US 10,287,619 B2
(45) Date of Patent: May 14, 2019

(54) MEASUREMENT METHOD FOR DEHYDROGENASE AND SUBSTRATE CONCENTRATION THEREOF, ELECTRON MEDIATOR, AND MEASUREMENT REAGENT FOR DEHYDROGENASE INCLUDING SAID ELECTRON MEDIATOR AND FOR SUBSTRATE THEREOF

(71) Applicant: Dojindo Laboratories, Mashiki-machi, Kamimashiki-gun (JP)

(72) Inventors: Masafumi Iwamoto, Mashiki-machi (JP); Tomoya Tanaka, Mashiki-machi (JP); Eiji Watanabe, Mashiki-machi (JP); Masanobu Shiga, Mashiki-machi (JP)

(73) Assignee: Dojindo Laboratories (JP)

( * ) Notice: Subject to any disclaimer, the term of this patent is extended or adjusted under 35 U.S.C. 154(b) by 0 days.

(21) Appl. No.: 15/304,710

(22) PCT Filed: Apr. 17, 2015

(86) PCT No.: PCT/JP2015/061805

§ 371 (c)(1),
(2) Date: Nov. 28, 2016

(87) PCT Pub. No.: WO2015/159969

PCT Pub. Date: Oct. 22, 2015

(65) Prior Publication Data

US 2017/0121753 A1 May 4, 2017

(30) Foreign Application Priority Data

Apr. 18, 2014 (JP) ................................ 2014-086180

(51) Int. Cl.
*C12Q 1/32* (2006.01)

(52) U.S. Cl.
CPC ......... *C12Q 1/32* (2013.01); *G01N 2333/904* (2013.01)

(58) Field of Classification Search
CPC ........................................................ C12Q 1/32
See application file for complete search history.

(56) References Cited

U.S. PATENT DOCUMENTS

| | | | |
|---|---|---|---|
| 5,122,244 A | 6/1992 | Hoenes et al. |
| 5,858,691 A | 1/1999 | Hoenes et al. |
| 8,535,511 B2 | 9/2013 | Wilsey et al. |
| 2014/0363835 A1 | 12/2014 | Chemnitius et al. |

FOREIGN PATENT DOCUMENTS

| | | | |
|---|---|---|---|
| EP | 2 636 750 A1 | 6/2012 | |
| JP | 61-087676 | 5/1986 | |
| JP | 02-100699 A | 4/1990 | |
| JP | 04-213051 A | 8/1992 | |
| JP | 09-005240 A | 1/1997 | |
| JP | 2005-523022 A | 8/2005 | |
| JP | 2011-515686 A | 5/2011 | |
| WO | WO 2003/089635 A1 | 10/2003 | |
| WO | WO 2009/118157 A1 | 10/2009 | |
| WO | WO-2009118157 A1 * | 10/2009 | ............ C12Q 1/004 |

OTHER PUBLICATIONS

Chan, et al., "Detection of Necrosis by Release of Lactate Dehydrogenase (LDH) Activity," Methods Mol Biol., vol. 979, pp. 65-70 (2013).

Yomo, T., et al., "Preparation and kinetic properties of 5-ethylphenazine—poly(ethylene glycol)—$NAD^+$ conjugate, a unique catalyst having an intramolecular reaction step," Eur. J. Biochem., 179, 299-305 (1989).

* cited by examiner

*Primary Examiner* — Noble E Jarrell
*Assistant Examiner* — John S Kenyon
(74) *Attorney, Agent, or Firm* — Fay Sharpe LLP

(57) ABSTRACT

A method for measuring concentration of dehydrogenase and substrate thereof in the presence of living cells, wherein an electron mediator that is hard to be reduced by living cells, for example, a compound represented by Formula (I), an electron mediator represented by the Formula (I) and a measurement reagent for dehydrogenase and substrate thereof including the electron mediator are disclosed.

A-L-M (I), wherein A represents a structural part containing at least one anionic group, M represents a structural part for mediating electron transfer and L represents a linker part for linking the A to the M.

16 Claims, 14 Drawing Sheets

MEASUREMENT METHOD FOR DEHYDROGENASE AND SUBSTRATE CONCENTRATION THEREOF, ELECTRON MEDIATOR, AND MEASUREMENT REAGENT FOR DEHYDROGENASE INCLUDING SAID ELECTRON MEDIATOR AND FOR SUBSTRATE THEREOF

This application claims the priority of PCT/JP2015/061805, filed on Apr. 17, 2015, and Japanese Patent Application No. 2014-86180, filed on Apr. 18, 2014, from which the PCT application claims priority, the disclosures of each of which are incorporated herein by reference in their entireties.

TECHNICAL FIELD

The present invention belongs to a technical field of measurement of concentrations of components in a cell culture or a blood and particularly relates to a measurement method for concentration of dehydrogenase and substrate thereof useful for a measurement of the dehydrogenase and the substrate thereof in the presence of living cells, an electron mediator used for the method and measurement reagent for dehydrogenase and substrate thereof including the electron mediator.

BACKGROUND ART

Detection system based on a substrate specific enzyme such as oxygenase and dehydrogenase is used for a measurement of a substrate such as glucose in a cell culture or a blood. In particular, the measurement system based on a dehydrogenase has highly valuable as it is hardly affected by oxygen in the atmosphere. Upon reacting the dehydrogenase with the substrate, a co-enzyme such as nicotine amide nucleotide (NAD) and nicotine amide dinucleotide phosphate (NADP) is reduced ($NAD^+ \rightarrow NADH$, $NADP^+ \rightarrow NADPH$). Concentration of the substrate can be determined from electric current or color intensity by transferring electron from the reduced form of the co-enzyme thus formed to an electrode or a reductive chromogenic dye via an electron mediator such as PMS (phenazine methosulfate), 1-Methoxy PMS (1-methoxy phenazine methosulfate) and PES (phenazine ethosulfate). Also, the concentration of the dehydrogenase can be determined using similar system by adding the substrate externally.

On the other hand, the electron mediator as mentioned above has a property to accept the electron from living cells. Various methods for measuring activities of living cells via the electron mediators that carry out electron transfer such as 1-Methoxy PMS and PES have been employed in a cell proliferation assay and cytotoxicity assay used in a drug screening in drug discovery and toxicity analysis for various substances. The method for evaluating the cytotoxicity by measuring the activity of the enzyme leaked out of the part of the dead cells into a culture medium via the electro mediators. However, the sample for the measurement has to be prepared by separating the living cells from the culture medium because the electron mediators as mentioned above also carries out the electron transfer with living cells (see F. K.-M. Chan et al., *Methods Mol. Biol.,* 2013, 979, 65-70.). The method in which the living cells are not separated is also proposed, however, the influence of the living cells cannot be avoided, which requires to lower the reaction temperature and shorten the reaction time (see JPA 2005-523022).

In the cytotoxicity assay, the method in which the dehydrogenase from dead cells is assayed using diaphorase, an enzyme mediating electron transfer, instead of low molecular electron mediator to suppress the electron transfer from the living cells is proposed. However, a reagent solution is of poor solubility and not easy for handling because of the use of the enzyme.

SUMMARY OF INVENTION

Problems to be Solved by the Invention

The object of the present invention is to solve the problem in the art as mentioned above and to provide a novel technology for measuring the concentration of the dehydrogenase and the substrate thereof in the present of living cells.

Means for Solving the Problem

An electron mediator is synthesized which does not mediate the electron transfer with the living cells and is capable of measuring the concentration of the dehydrogenase and the substrate thereof even in the presence of the living cells as a result of intensive investigation.

In a first aspect of the present invention the problem as mentioned above is solved by providing a measurement method for concentration of dehydrogenase and substrate thereof in the presence of living cells, wherein an electron mediator that is hard to be reduced by living cells is used.

In the measurement method according to the first aspect of the present invention, the electron mediator that is hard to be reduced by the living cells is preferably a compound represented by Formula (I) shown below:

$$A\text{–}L\text{–}M \qquad (I)$$

In the Formula (I), A represents a structural part containing at least one anionic group, M represents a structural part for mediating electron transfer and L represents a linker part for linking the A of the M.

In the measurement method according to the first aspect of the present invention, the structural part for mediating electron transfer M may be that represented by Formula (II) shown below:

(II)

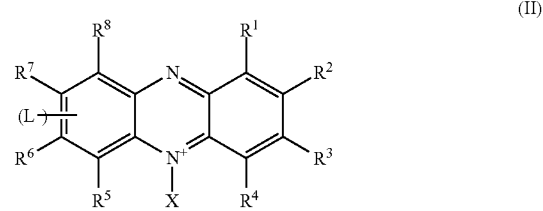

In Formula (II), X represents alkyl group, alkyl sulfuric acid group or alkyl sulfonic acid group having 1 to 5 carbon atoms that may be branched, $R^1$, $R^2$, $R^3$, $R^4$, $R^5$, $R^6$, $R^7$ and $R^8$ independently represent a hydrogen atom, an alkyl group or an alkoxy group having 1 to 5 carbon atoms that may be branched, a hydroxyl group or halogen atom or nitro group or amino group that may be substituted and any one of $R^1$ to $R^7$ is the linker part L.

A second aspect of the present invention solves the problem as mentioned above by providing an electron mediator represented by Formula (I) shown above.

In the electron mediator according to the second aspect of the present invention, the structural part for mediating electron transfer M may be that represented by Formula (II) shown above.

In the measurement method according to the first aspect of the present invention, the structural part for mediating electron transfer M may be that represented by any one of Formula (I-1) to (I-16) shown below.

I-1

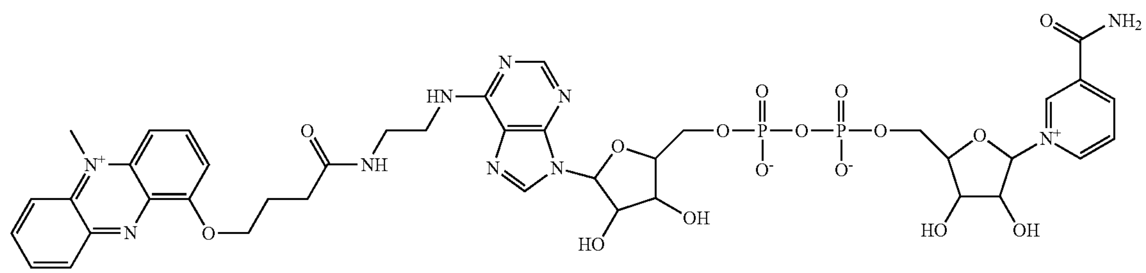

I-2

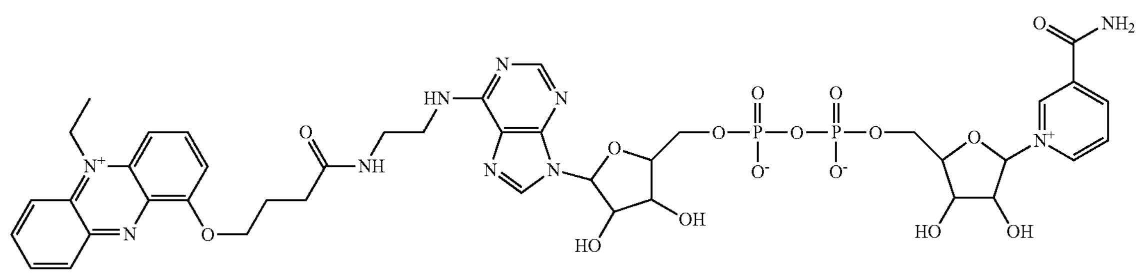

I-3

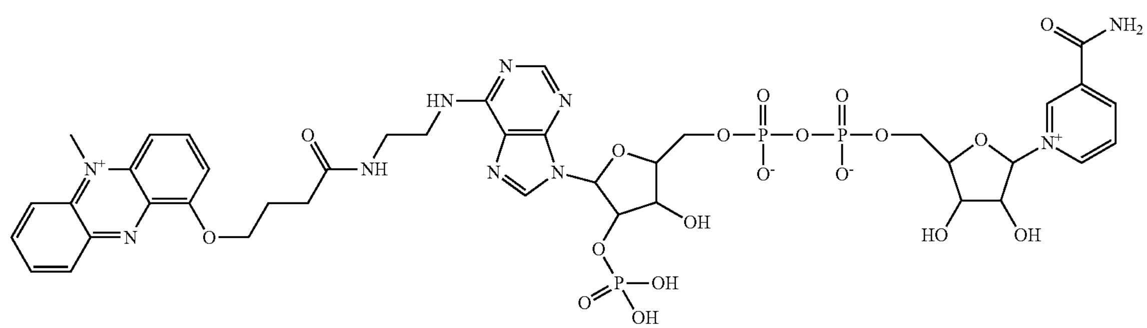

I-4

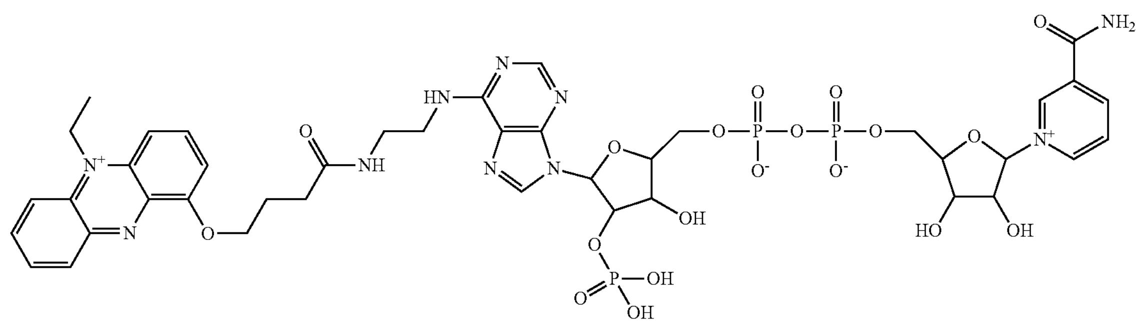

I-5

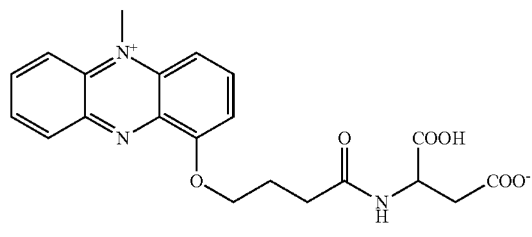

I-6

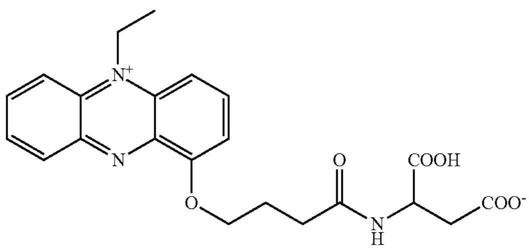

-continued

I-7

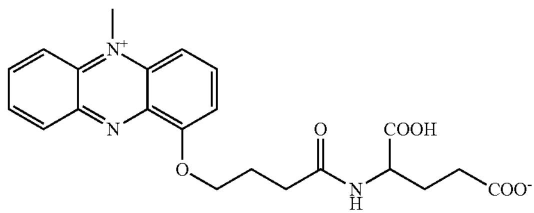

I-8

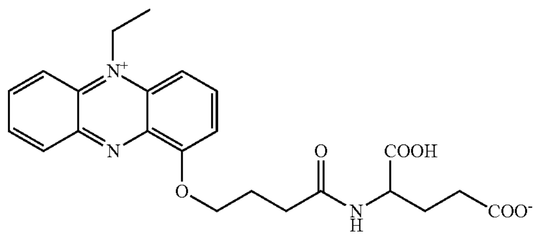

I-9

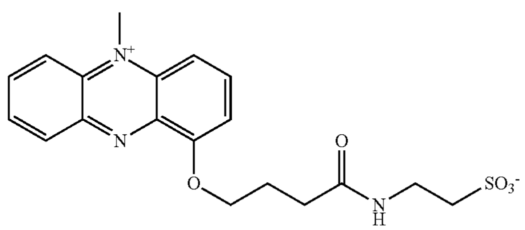

I-10

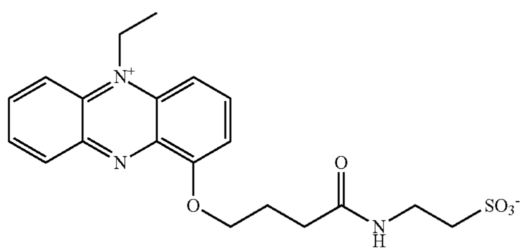

I-11

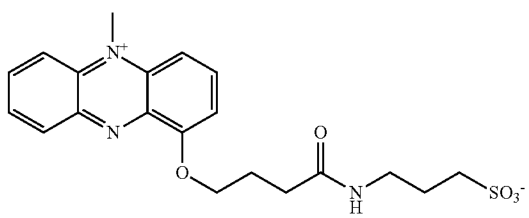

I-12

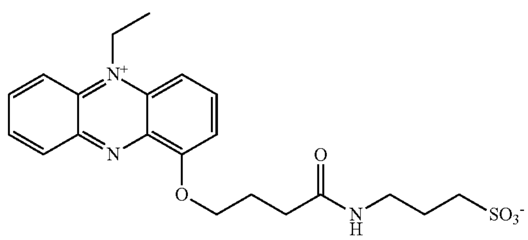

I-13

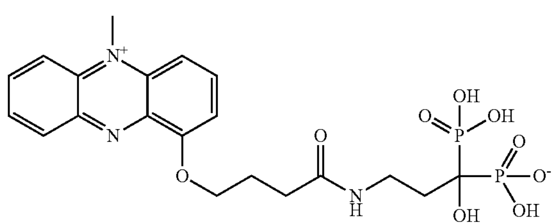

I-14

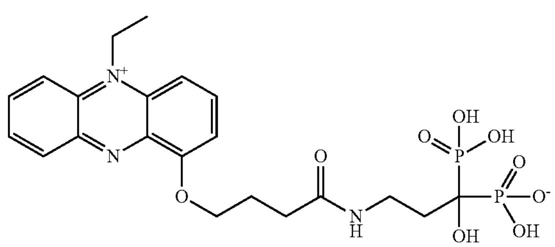

I-15

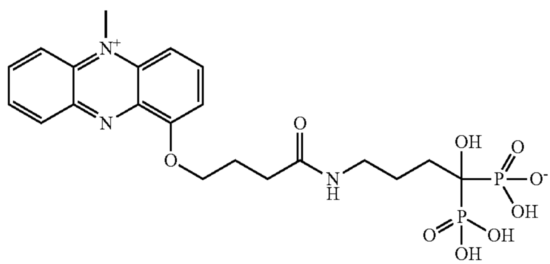

I-16

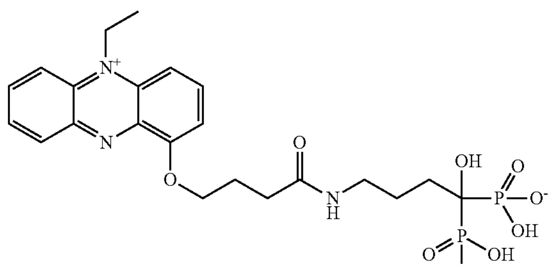

A third aspect of the present invention solves the problem as mentioned above by providing a measurement reagent for dehydrogenase and substrate thereof comprising the electron mediator according to the second aspect of the present invention.

In the measurement reagent according to the third aspect of the present invention, the measurement reagent may be that for lactate dehydrogenase.

Effect of the Invention

By using the measurement method for concentration of dehydrogenase and substrate thereof, the electron mediator, and the measurement reagent for dehydrogenase and substrate thereof including the electron mediator according to the present invention, no significant electron transfer takes place between the living cells and the electron mediator. Therefore, the measurement of the concentration of dehydrogenase and the substrate thereof may be conducted in the presence of the living cells without separation.

EMBODIMENT OF THE INVENTION

Figure 1A:
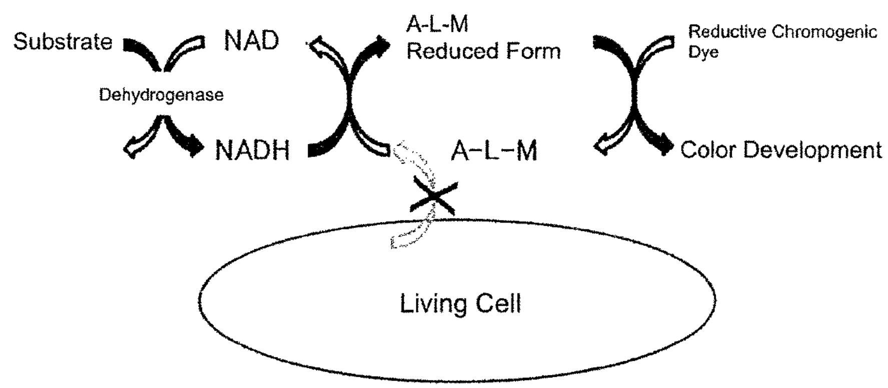
FIG. 1A and FIG. 1B show schematic diagrams illustrating a principle of the measurement of the concentration of the dehydrogenase and the substrate thereof in the presence of the living cells according to the present invention in comparison with the prior art.
Figure 1B:
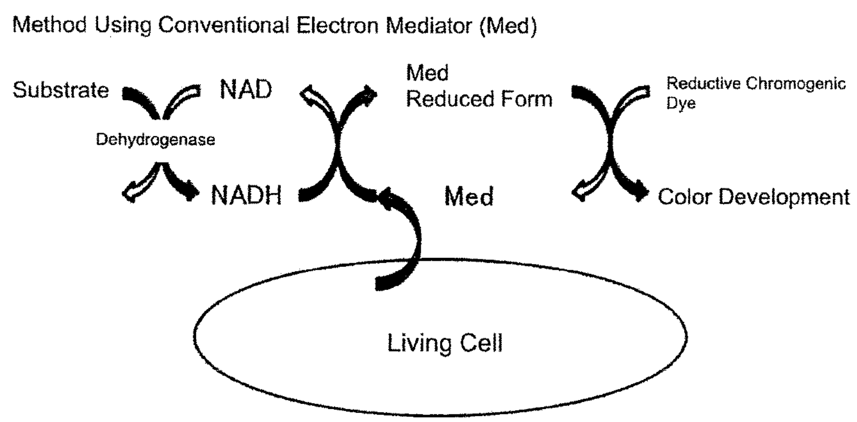

In the measurement method for concentration of dehydrogenase and substrate thereof according to the first embodiment of the present invention (hereinafter, it may be abbreviated to "the measurement method"), the electron mediator according to the second embodiment of the present invention represented by Formula (I) as shown below (an example of the electron mediator that is hard to be reduced by the living cells; hereinafter it may be abbreviated to "the electron mediator") is used.

$$A\text{–}L\text{–}M \quad (I)$$

In the Formula (I), A represents a structural part containing at least one anionic group, M represents a structural part for mediating electron transfer and L represents a linker part for linking the A of the M.

In the Formula (I), the A comprises at least one structural part containing at least one anionic group. The anionic group imparts the property that the electron mediator does not mediate the electron transfer with the living cells.

The A is not particularly limited and examples include amino acids such as aspartic acid and glutamic acid; amino sulfonic acid such as taurine and homotaurine; amino phosphoric acid such as pamidronic acid and alendronic acid; and nucleotides such as nicotine amide dinucleotide and nicotine amide dinucleotide phosphate.

In the Formula (I) as shown above, the M represents an oxidized form of the structural part which may serve as the electron mediator. The oxidized form of the structural part mediates the electron transfer and it may adopt the structure of oxidized/reduced form.

As the oxidized form of the structural part represented by the Formula (I), in principle, a component of the electron mediator, structural part contained in various structures conventionally used for the detection of the dehydrogenase and the substrates thereof, in which the moiety having phenazinium structure represented by Formula (II) as shown below is particularly preferred.

(II)

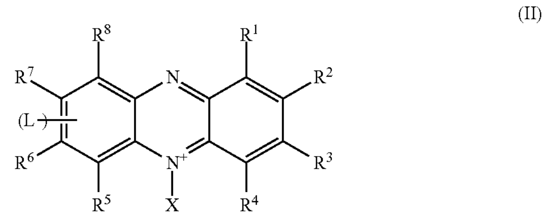

In the Formula (II), X represents alkyl group, alkyl sulfuric acid group or alkyl sulfonic acid group having 1 to 5 carbon atoms that may be branched, $R^1$, $R^2$, $R^3$, $R^4$, $R^5$, $R^6$, $R^7$ and $R^8$ independently represent hydrogen atom, alkyl group or alkoxy group having 1 to 5 carbon atom that may be branched, hydroxyl group or halogen atom or nitro group or amino group that may be substituted. In the Formula (II), L refers to a linker part (to be mentioned below) and any one of $R^1$ to $R^7$ is the linker part L.

In the Formulae (I) and (II) as shown above, the L represents the linker part for linking the A (the structural part containing at least one anionic group) and the M (the structural part for mediating electron transfer). The structure of the linker part is not particularly limited.

Preferred examples of the compound represented by the Formula (I), a component of the electron mediator include the compounds represented by Formulae (I-1) to (I-16), however, the electron mediator is not limited by them.

I-1

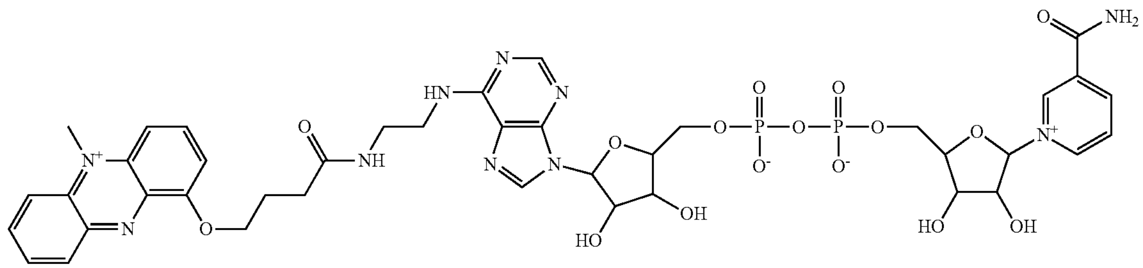

-continued
I-2
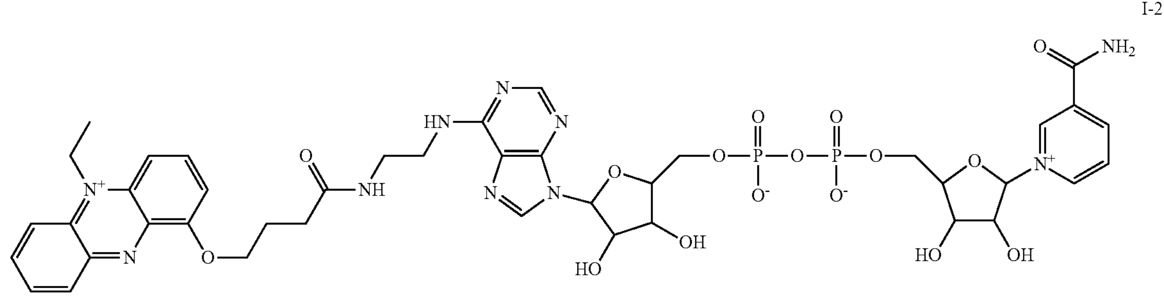
I-3
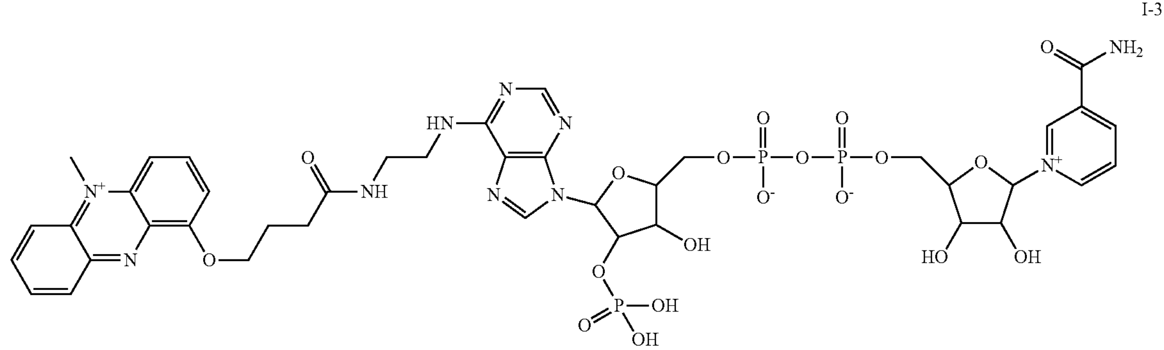
I-4
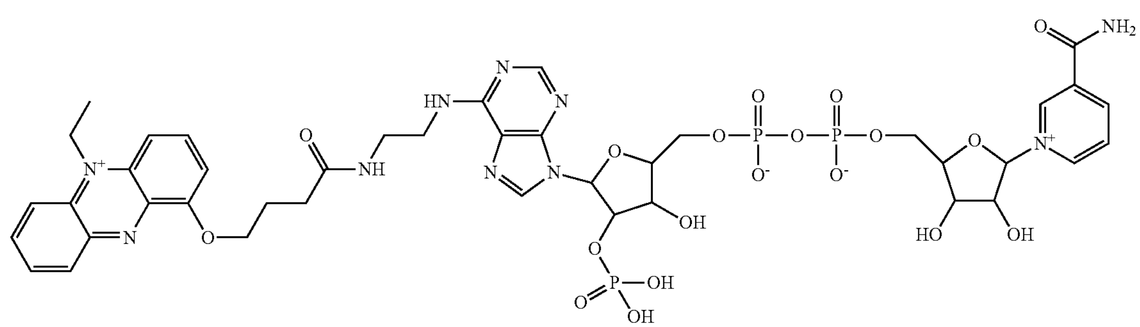
I-5 I-6
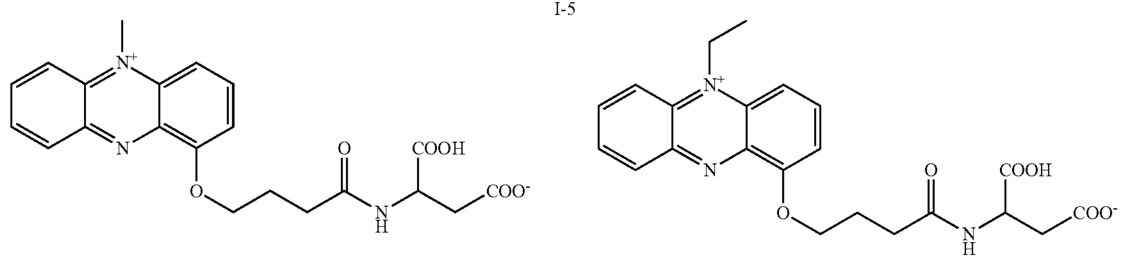
I-7 I-8
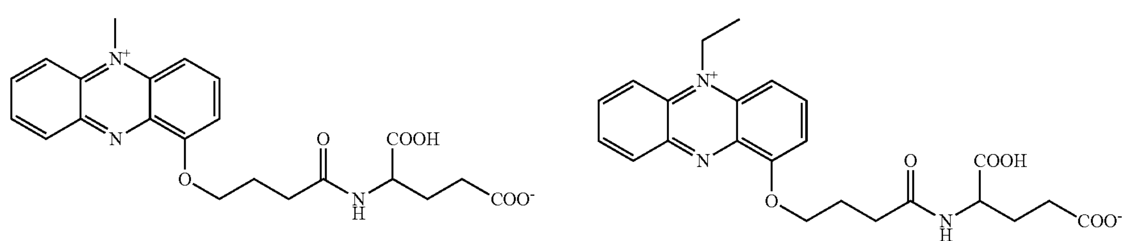

-continued

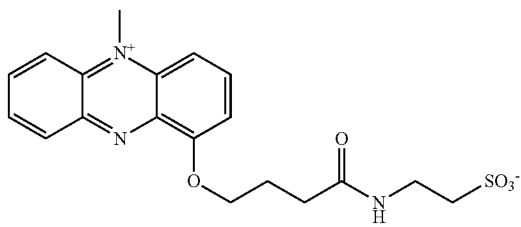

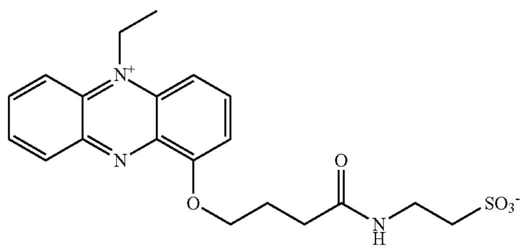

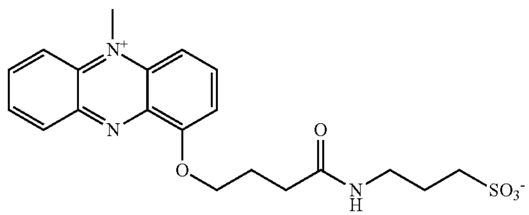

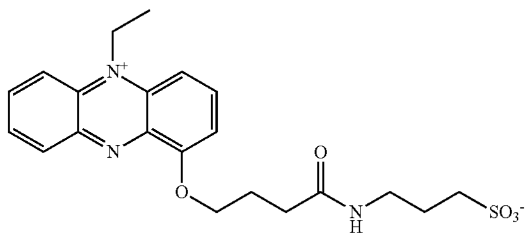

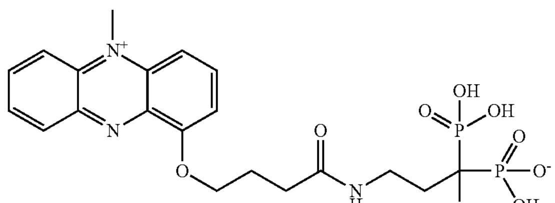

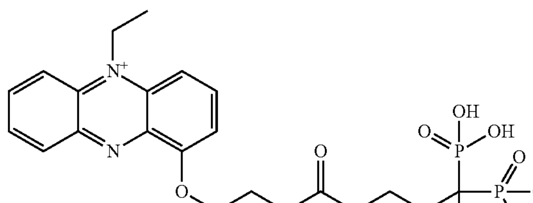

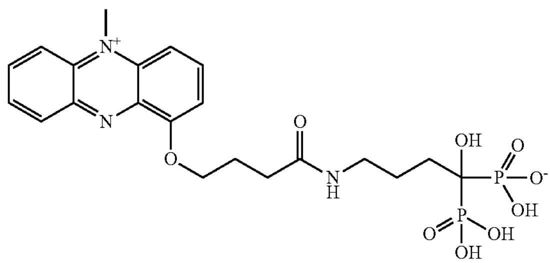

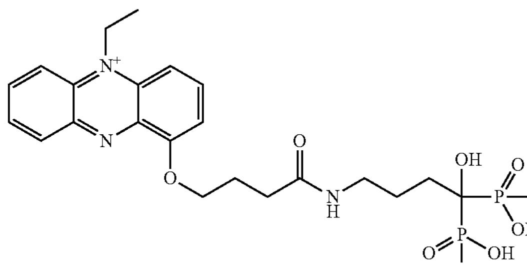

Thus, according to the present invention, as a different aspect of the present invention, a quantitative measurement method for concentration of dehydrogenase and substrate thereof in a cell culture medium or a blood sample possibly containing living cells by adding the electron mediator consisting of the compound represented by the Formula (I) and a reductive chromogenic dye, a measurement reagent for the dehydrogenase and the substrate thereof used for the method containing the electron mediator consisting of the compound represented by the Formula (I) and a reductive chromogenic dye are provided.

The reductive chromogenic dye used for the measurement method for the concentration of the dehydrogenase and the substrate thereof according to the first embodiment of the present invention is a compound that acts as an electron acceptor and the compound itself reduced to develop (change) a color. Preferred examples of the reductive chromogenic dye are various tetrazolium salt, which is readily reduced to formazan to develop the color. Particularly preferred tetrazolium salt is the compound referred to as WST represented by Formula (III) shown below that forms water soluble formazan of high sensitivity of which absorbance at 430 nm to 490 nm. The reductive chromogenic dye is not limited to the tetrazolium salt and, in addition, for example, resazurin and the like may also be used.

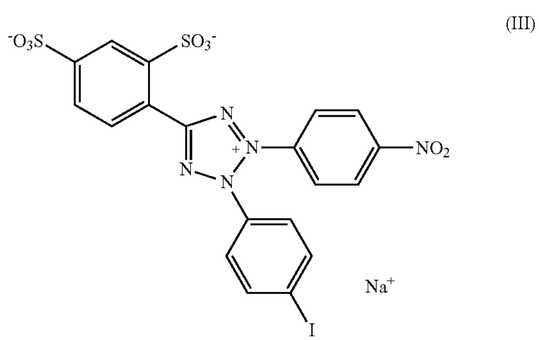

-continued

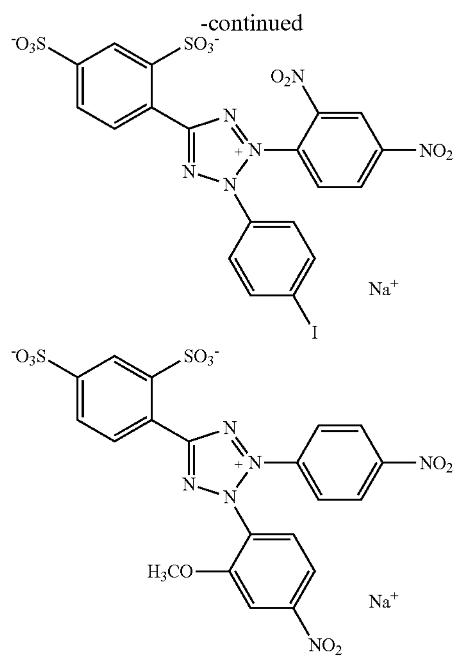

Figure 2A:
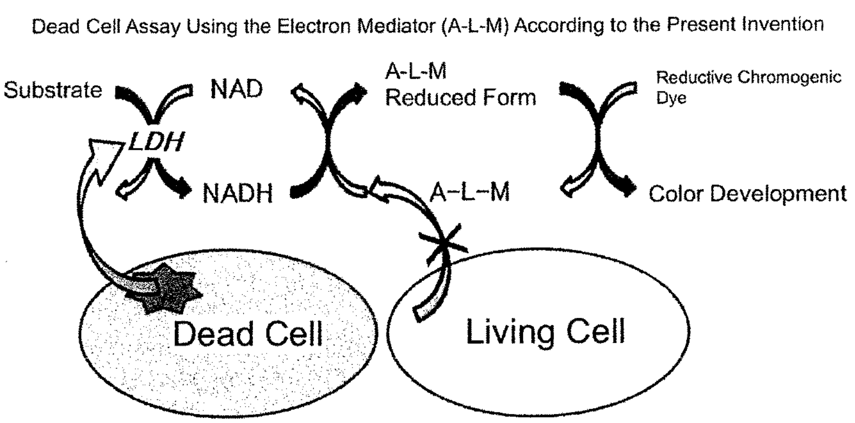
FIG. 2A and FIG. 2B show schematic diagrams illustrating a principle of the dead cell assay measuring the concentration of the dehydrogenase leaked out of the dead cells in the presence of the living cells according to the present invention in comparison with the prior art.
Figure 2B:
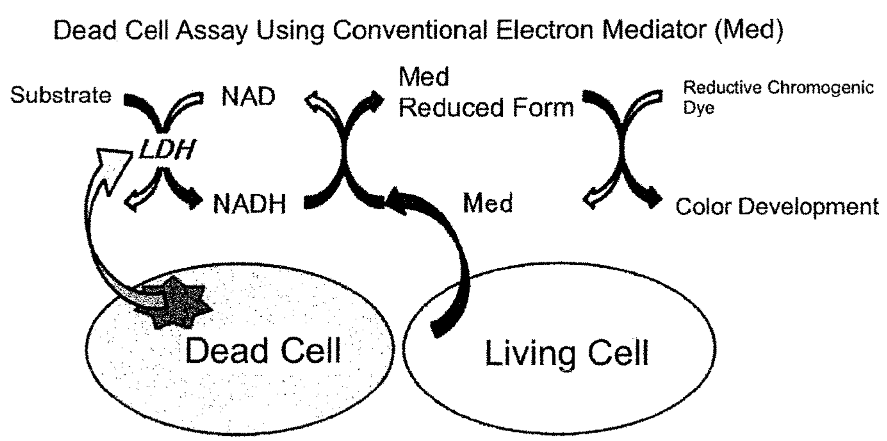
Figure 3A:
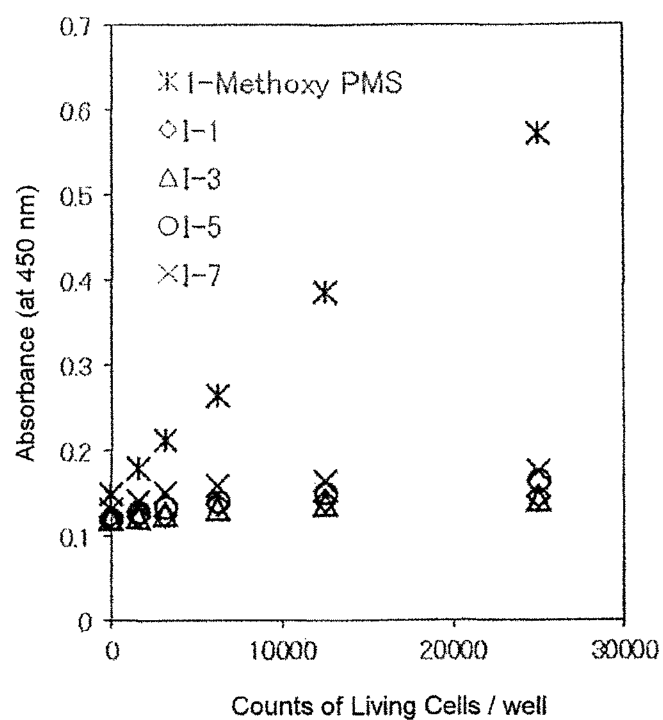
FIG. 3A, FIG. 3B, FIG. 3C and FIG. 3D show a difference of the electron mediator according to the present invention from the conventional electron mediator with respect to the electron transfer with the living cells.
Figure 3B:
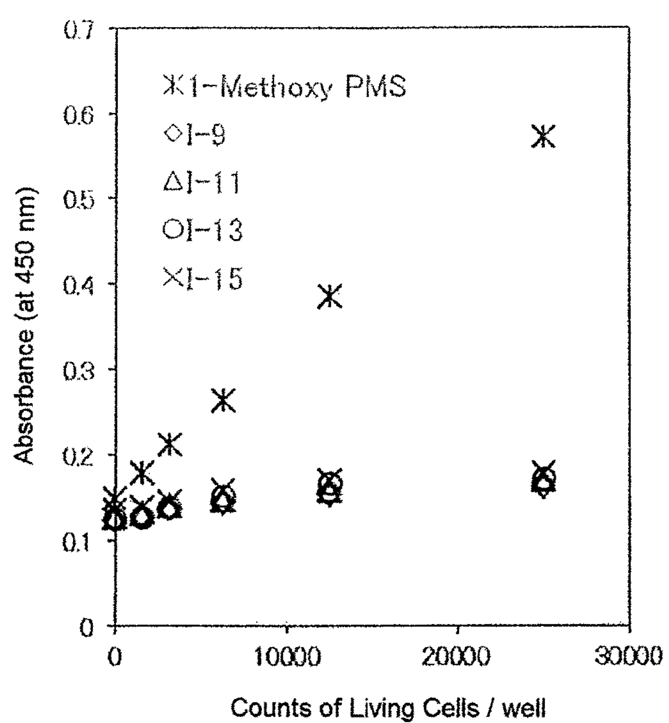
Figure 3C:
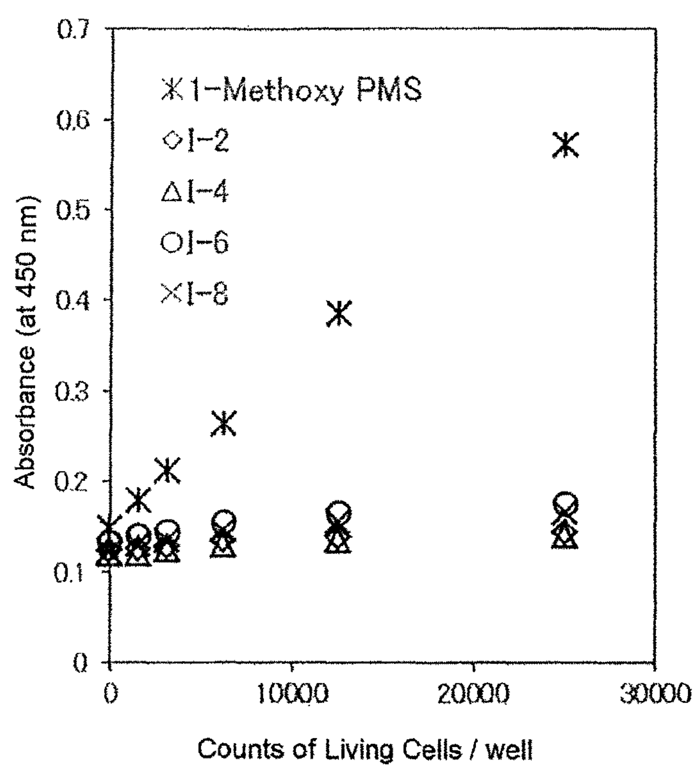
Figure 3D:
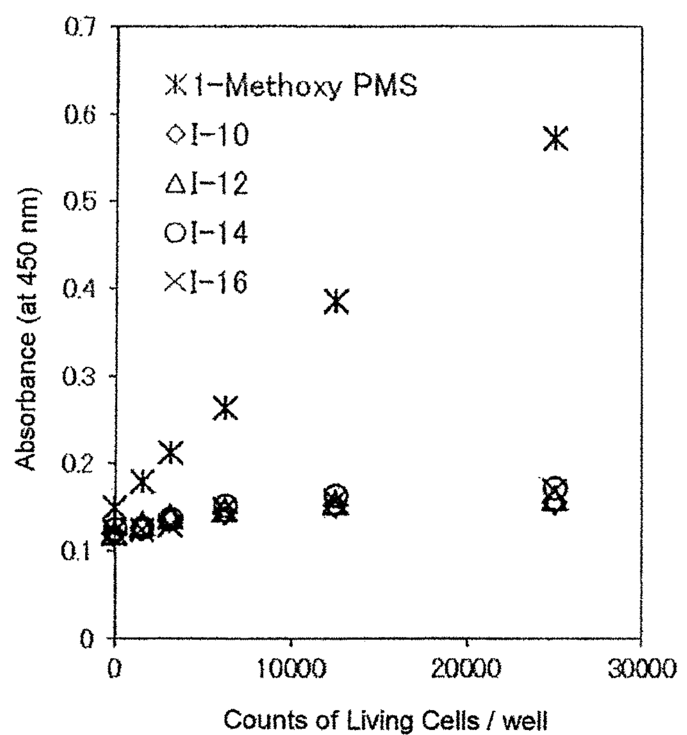
Figure 4A:
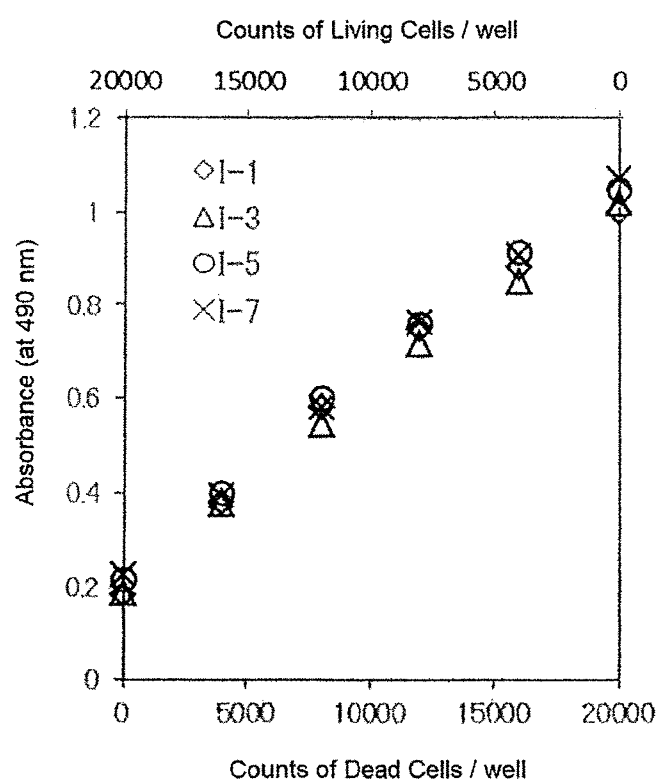
FIG. 4A, FIG. 4B, FIG. 4C and FIG. 4D show a dead-cell dependent chromogenic reaction of the electron mediator according to the present invention in the presence of the living cells.
Figure 4B:
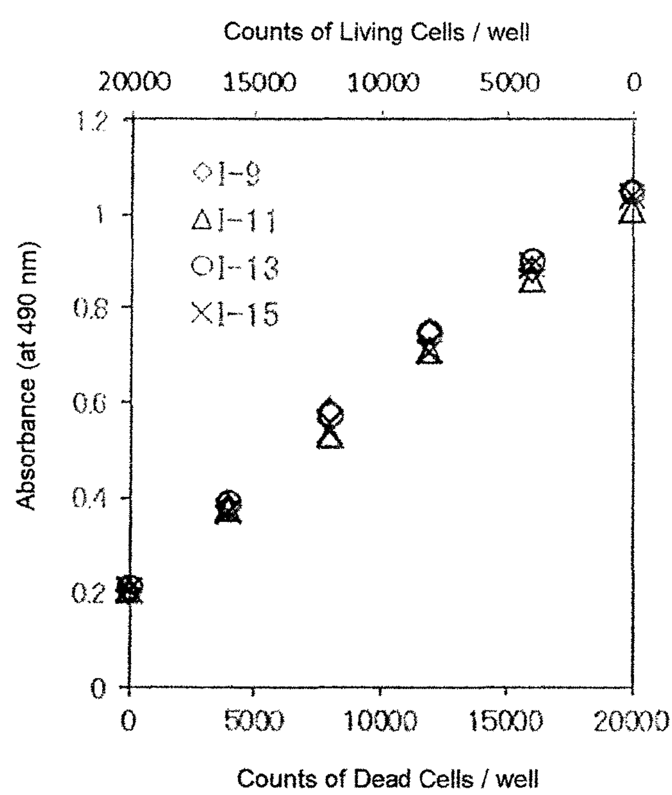
Figure 4C:
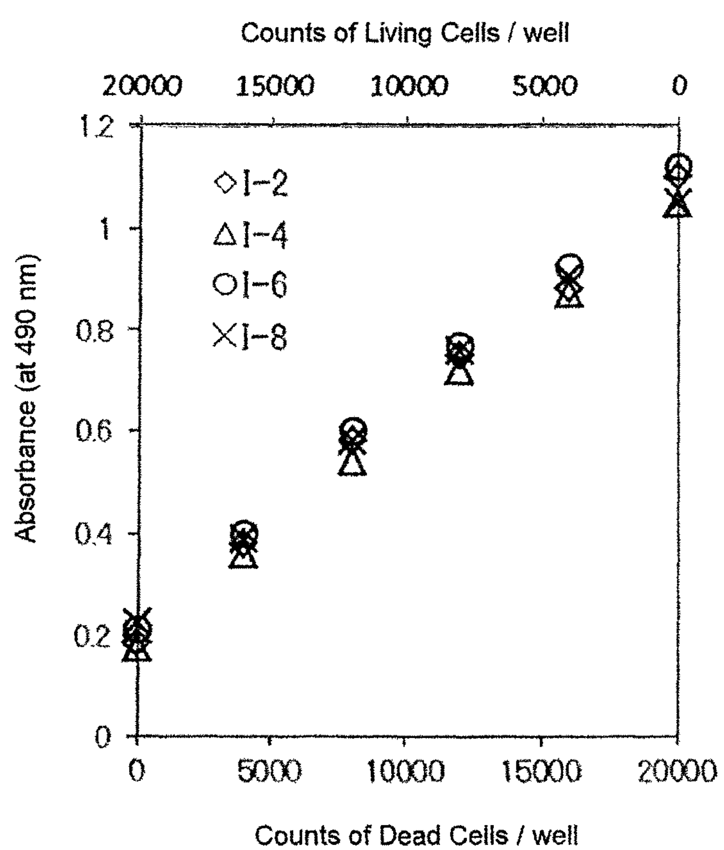
Figure 4D:
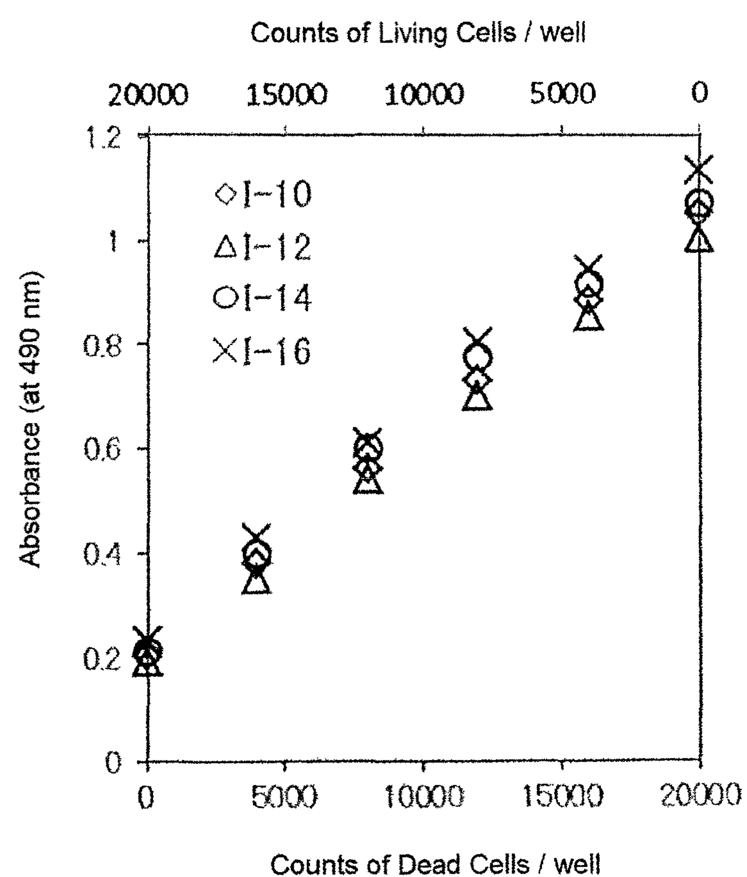

An example of the measurement according to the present invention includes a dead cell assay using lactate dehydrogenase (LDH) leaked out of the dead cells as an index. FIG. 2A and FIG. 2B schematically show a principle of the dead cell assay even in the presence of the living cells in comparison with the prior art.

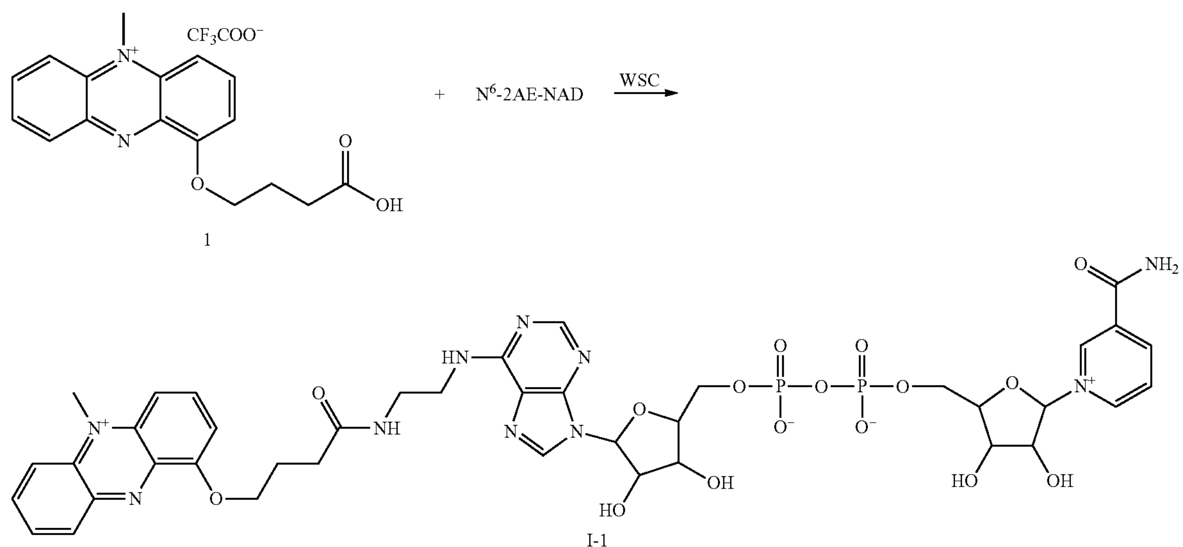

As shown in FIG. 2B, when the conventional electron mediator that carries out the electron transfer with the living cells (MED: for example, 1-Methoxy PMS and PES); lactate, the substrate; NAD, a co-enzyme and the reductive chromogenic dye are added to a cell sample (a cell culture medium), LDH leaked out of the dead cells catalyzes a dehydrogenation of lactate and color development takes place as a result of subsequent reduction of NAD, reduction of Med and reduction of the reductive chromogenic dye (such as WST-8). In addition, the color development of WST-8 also takes place through the reduction of the Med by NADH in the living cells. For that reason, dead cells cannot be assayed selectively. Therefore, in the conventional art, separation of the living cells by transferring a part of the culture medium to another plate prior to the measurement, centrifuging the floating cells prior to the measurement and the like is required.

Whereas, in the measurement method according to the first embodiment of the present invention shown in FIG. 2A, LDH from the dead cells may be assayed even in the presence of the living cells as the electron mediator is hard to be reduced by NADH in the living cells. As mentioned above, according to the present invention, the dead cells may be assayed by simply adding a chromogenic solution (comprising the compound represented by the formula A-L-M, the substrate, the co-enzyme and the reductive chromogenic dye) in the presence of the living cells without transferring a part of the culture medium to another plate or centrifuging the floating cells. Also the chromogenic solution is highly stable as it does not contain the electron transfer enzyme, a protein, which allows long term preservation as the solution. In conclusion, the technology for assaying the dead cells according to the present invention is particularly useful for large-scale and rapid cytotoxicity screening of candidate drug in the drug discovery research.

EXAMPLES

Examples will be shown below for illustrating the characteristics of the present invention, however, the present invention is not particularly limited to these Examples.

Example 1: Synthesis of I-1

5-Methyl-1-carboxybutyl phenazine derivative (1) was synthesized according to the method described in WO 2009/118157. 40 mg (57 μmol) of $N^6$-2AE-NAD (Dojindo Molecular Technologies, Inc.) was dissolved in 1 mL of 100 mmol/L phosphate buffer (pH 7.4), 40 mg (209 μmol) of WSC (1-Ethyl-3-(3-dimethylaminopropyl) carbodiimide hydrochloride) and 85.8 mg (209 μmol) of compound 1 were added and reacted at room temperature for 20 hours. The reaction mixture was purified with a reverse phase HPLC and vacuum dried in a desiccator to afford 12 mg of red solid of compound I-1.

Example 2: Synthesis of I-4

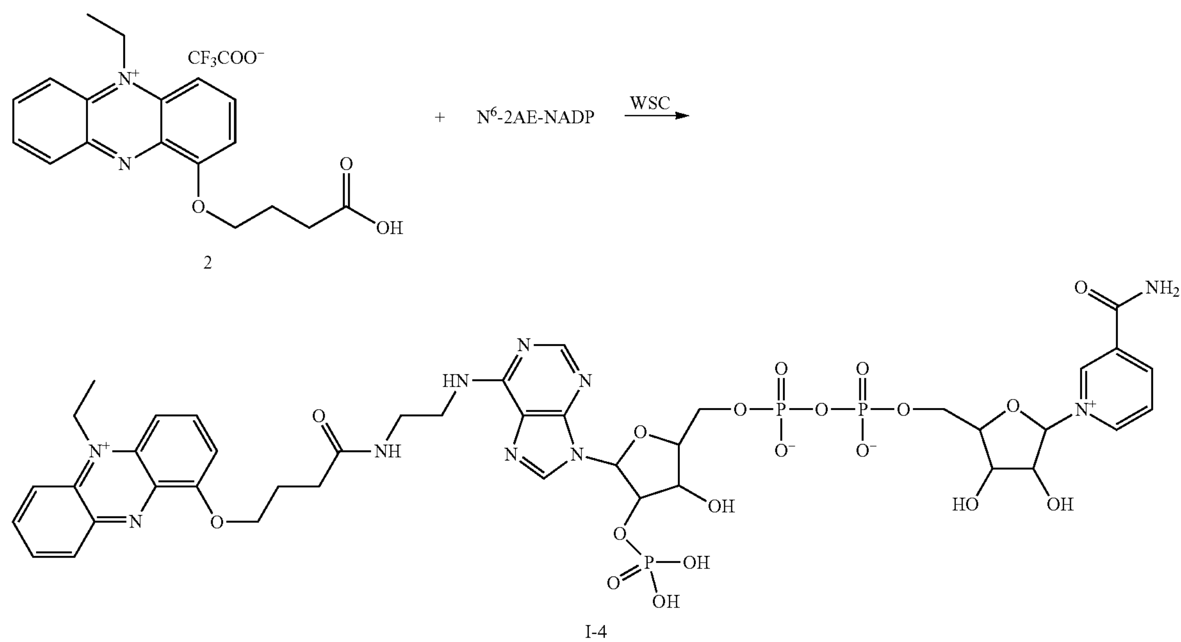

5-Ethyl-1-carboxybutyl phenazine derivative (2) was synthesized according to the method described in WO 2009/118157. 44.8 mg (57 μmop of $N^6$-2AE-NAD (Dojindo Molecular Technologies, Inc.) was dissolved in 1 mL of 100 mmol/L phosphate buffer (pH 7.4), 40 mg (209 μmop of WSC (1-Ethyl-3-(3-dimethylaminopropyl) carbodiimide hydrochloride) and 88.7 mg (209 μmop of compound 2 were added and reacted at room temperature for 20 hours. The reaction mixture was purified with a reverse phase HPLC and vacuum dried in a desiccator to afford 15 mg of red solid of compound I-4.

Example 3: Synthesis of I-6

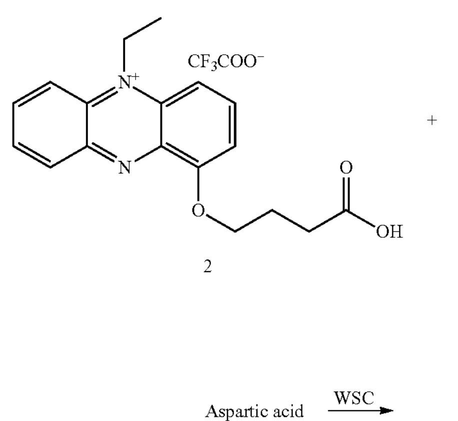

Aspartic acid $\xrightarrow{\text{WSC}}$

-continued

I-6

5-Ethyl-1-carboxybutyl phenazine derivative (2) was synthesized according to the method described in WO 2009/118157. 40 mg (301 μmol) of aspartic acid was dissolved in 1 mL of 100 mmol/L phosphate buffer (pH 7.4), 40 mg (209 μmol) of WSC (1-Ethyl-3-(3-dimethylaminopropyl) carbodiimide hydrochloride) and 88.7 mg (209 μmol) of compound 2 were added and reacted at room temperature for 20 hours. The reaction mixture was purified with a reverse phase HPLC and vacuum dried in a desiccator to afford 45 mg of red solid of compound I-6.

Example 4: Synthesis of I-10

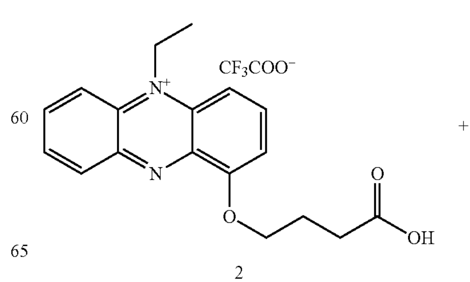

2

-continued

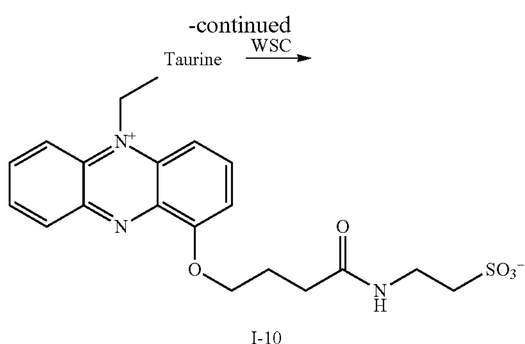

I-10

5-Ethyl-1-carboxybutyl phenazine derivative (2) was synthesized according to the method described in WO 2009/118157. 40 mg (320 μmol) of taurine was dissolved in 1 mL of 100 mmol/L phosphate buffer (pH 7.4), 40 mg (209 μmol) of WSC (1-Ethyl-3-(3-dimethylaminopropyl) carbodiimide hydrochloride) and 88.7 mg (209 μmol) of compound 2 were added and reacted at room temperature for 20 hours. The reaction mixture was purified with a reverse phase HPLC and vacuum dried in a desiccator to afford 50 mg of red solid of compound I-10.

Example 5: Synthesis of I-15

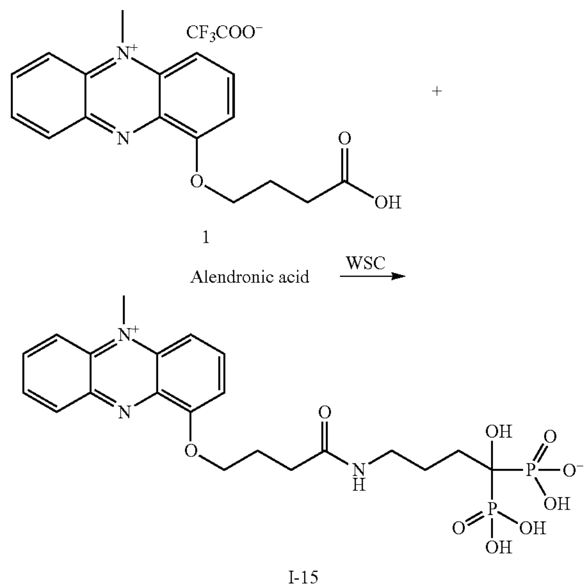

I-15

5-Methyl-1-carboxybutyl phenazine derivative (1) was synthesized according to the method described in WO 2009/118157. 75 mg (301 μmol) of alendronic acid was dissolved in 1 mL of 100 mmol/L phosphate buffer (pH 7.4), 40 mg (209 μmol) of WSC (1-Ethyl-3-(3-dimethylaminopropyl) carbodiimide hydrochloride) and 85.8 mg (209 μmol) of compound 1 were added and reacted at room temperature for 20 hours. The reaction mixture was purified with a reverse phase HPLC and vacuum dried in a desiccator to afford 40 mg of red solid of compound I-15.

Example 6: Evaluation of Electron Transfer with Living Cells

Examples of the evaluation of the electron transfer between the electron mediators and the living cells are shown. For comparison, a similar experiment was carried out using 1-Methoxy PMS, a known electron mediator that carries out electron transfer with the living cells. Human myeloid leukemia cells (HL60) were seeded on a 96 well microplate at 25,000 to 0 cells/well, the measurement reagent was added at a final concentration shown below, after reacting at 37° C. for 3 hours and absorbance at 450 nm was measured.

Final concentration of the measurement reagent: WST-8 (500 μM), the electron mediator (10 μM).

The results of the measurements are shown in FIG. 3A, FIG. 3B, FIG. 3C and FIG. 3D. When 1-Methoxy PMS is used, 1-Methoxy PMS accepts electron from the living cells, reduces the WST-8 to form formazan, a yellow dye, which results in an increasing of absorbance. In contrast, when any derivatives of the electron mediator according to the present invention is used, formation of the formazan attributed to the living cells is significantly suppressed compared with 1-Methoxy PMS.

Example 7: Assay of LDH from Dead Cells in the Presence of Living Cells

Human myeloid leukemia cells (HL60) after counting the cell number by a hemocytometer was divided into two groups, one of which were killed by freezing and thawing (dead cell sample). The rest (living cell sample) and the dead cell sample were mixed in different ratios to prepare samples of similar total cell counts and different ratios of the dead cells and the living cells.

Lactic acid, the substrate of LDH, the reductive chromogenic dye, the co-enzyme and the electron mediator was added at final concentrations shown below, after reacting at room temperature for 15 minutes and absorbance at 450 nm was measured.

Final concentration of the reagents: lactic acid (0.375%), WST-8 (500 μM), NAD (10 μM), the electron mediator (10 μM).

The results of the measurement are shown in FIG. 4A, FIG. 4B, FIG. 4C and FIG. 4D. In the horizontal axis, the living cell counts is 20,000 at the point of the dead cell counts of 0, 10,000 at the point of the dead cell counts of 10,000 and 0 at the point of the dead cell counts of 20,000. The graph obtained for any derivatives of the electron mediator according to the present invention shows linear increase in the absorbance to the dead cell counts, which shows that the results are not significantly affected by the living cells.

Example 8: Cytotoxicity Assay Using the Dead Cells as an Index

The example of the cytotoxicity assay using the LDH leaked out of the dead cell as an index and the solutions of the chromogenic reagent prepared using the electron mediator according to the present invention is shown. As a model of the cytotoxicity assay, cytotoxicity of mitomycin C (MMC) against Chinese Hamster Ovarian (CHO) cells was assayed.

A suspension of the CHO cells at the concentration of $1.5\times10^5$ cells/mL was prepared using serum-containing medium and 100 μL of the suspension was seeded to each well of a 96 well microplate. After incubating at 37° C. for 4 hours in a $CO_2$ incubator, 10 μL of MMC was added at final concentration of 1 mM to 0.0001 mM. The microplate was incubated at 37° C. for 20 hours in the $CO_2$ incubator. In order to assay the color development of the sample in which all cells were dead, Triton X-100 was added to a part of the wells to kill the cells entirely. 10 μL of the chromogenic solution (prepared at the concentration as shown in Example 7) was added to each cell. After incubating at 37° C. for 20 minutes in a $CO_2$ incubator, the absorbance at 450 nm was measured using a microplate reader.

A comparative experiment using a commercially available dead cell assay kit (BioPioneer Inc., LDH-Cytotoxicity Assay Kit) using LDH as an index. The kit was used according to the protocol attached to the product. The measurement method of the absorbance was similar to that as mentioned above except that supernatant of the medium was taken and transferred to another plate so as not to be contaminated with the living cells upon conducting the chromogenic reaction.

Figure 5A:
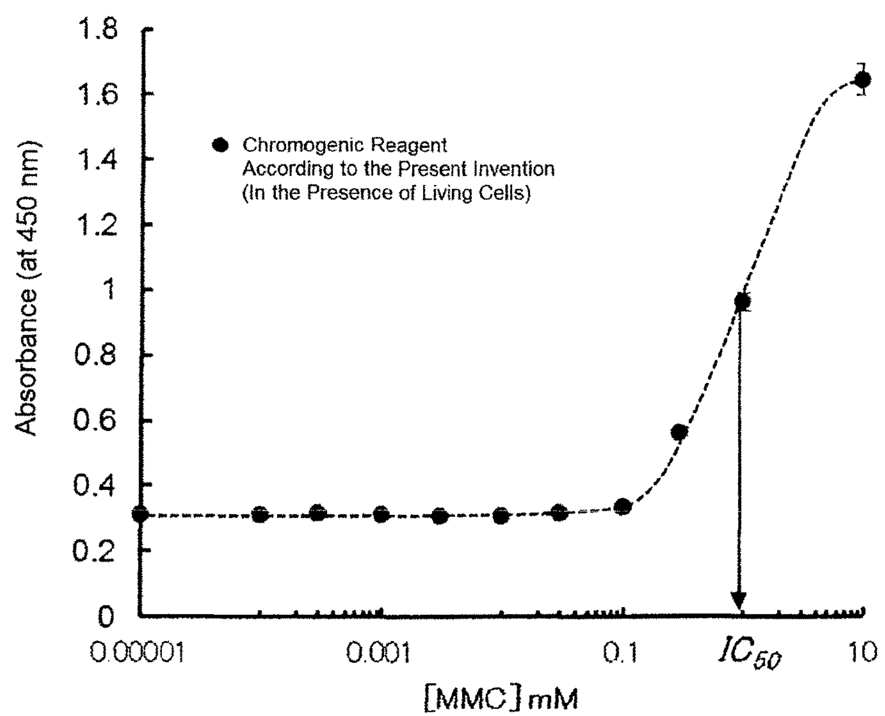
FIG. 5A and FIG. 5B show a comparison of the dead cell assay based on LDH from the dead cells as an index using the electron mediator according to the present invention with the dead cell assay using the conventional product that requires separation of the living cells.
Figure 5B:
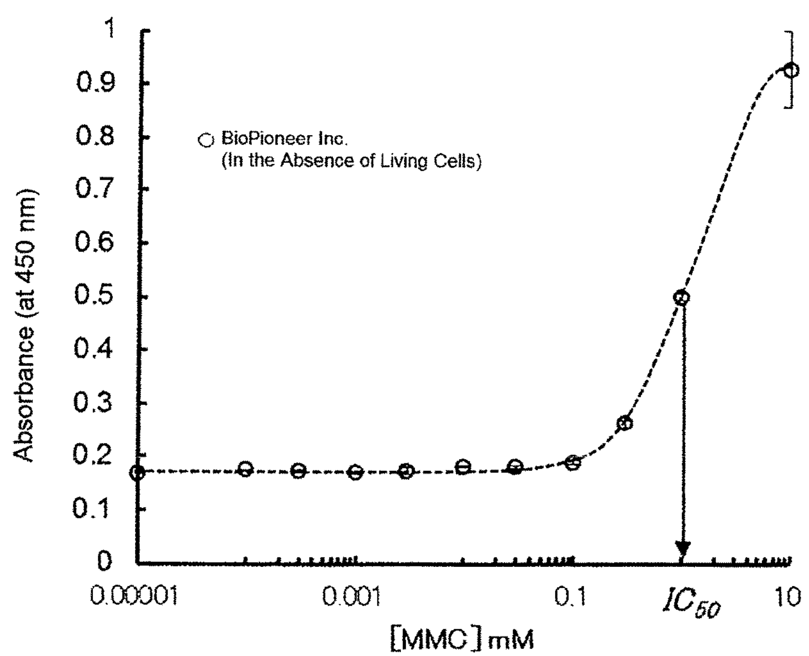

The results of the measurements are shown in FIG. 5A and FIG. 5B. No difference was observed between the values of 50% Inhibition concentration ($IC_{50}$) of mitomycin C against the CHO cell showing the cytotoxicity obtained using the electron mediator according to the present invention (see FIG. 5A) and obtained using the conventional product accepted as the dead cell assay (see FIG. 5B), which showed that the electron mediator according to the present invention may be applicable to the assay of the dead cells in the presence of the living cells.

The example of the assay of the concentration of the dehydrogenase is shown above, however, not only the concentration of the dehydrogenase, the measurement of the concentration of the substrate of the dehydrogenase is also possible in principle. Thus, using the compound according to the present invention, the concentration of the dehydrogenase and the substrate thereof may be assayed even in the presence of the living cells.

The present invention is, without departing from the broader spirit and scope of the present invention, in which are capable of various embodiments and modifications. Further, the above-described embodiments are intended to illustrate the present invention and are not intended to limit the scope of the present invention. In other words, the scope of the present invention, not the embodiments, illustrated by the appended claims. The various modifications to be applied within the scope in and meaning equivalent invention and its claims are considered within the scope of the present invention.

The invention claimed is:

1. A measurement method for concentration of a dehydrogenase and substrate thereof in the presence of living cells, comprising adding a chromogenic solution to a cell sample containing the dehydrogenase or a substrate for the dehydrogenase and living cells, the chromogenic solution comprising an electron mediator that is hard to be reduced by living cells, the dehydrogenase or the substrate for the dehydrogenase, and a reductive chromogenic dye; and detecting a color change resulting from reduction of the chromogenic dye, wherein the electron mediator is a compound represented by Formula (I):

A-L-M (I), wherein A represents a structural part containing at least one anionic group selected from amino acids, amino sulfonic acids, amino phosphonic acid, and nucleotides, M represents a structural part for mediating electron transfer, and L represents a linker part for linking the A and the M, wherein L is an alkoxy group, and wherein M is represented by Formula (II):

(II)

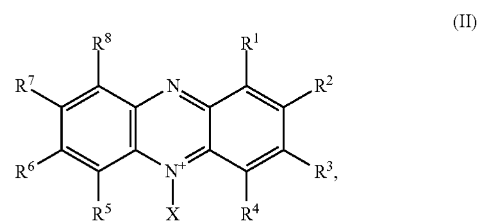

wherein X represents an alkyl group, an alkyl sulfuric acid group or an alkyl sulfonic acid group having 1 to 5 carbon atoms that may be branched, $R^1$, $R^2$, $R^3$, $R^4$, $R^5$, $R^6$, $R^7$, and $R^8$ independently represent a hydrogen atom, an alkyl group or an alkoxy group having 1 to 5 carbon atoms that may be branched, a hydroxyl group or a halogen atom or a nitro group or an amino group that may be substituted, and wherein any one of $R^1$ to $R^7$ is the linker part L.

2. An electron mediator represented by Formula (I):

A-L-M (I), wherein A represents a structural part containing at least one anionic group selected from amino acids, amino sulfonic acids, amino phosphonic acid, and nucleotides;

M represents a structural part for mediating electron transfer, and

L represents a linker part for linking the A and the M, the linker part being an alkoxy group having 1 to 5 carbon atoms;

wherein M is represented Formula (II):

(II)

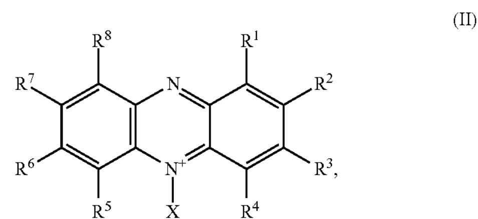

wherein X represents an alkyl group, an alkyl sulfuric acid group or an alkyl sulfonic acid group having 1 to 5 carbon atoms that may be branched, $R^1$, $R^2$, $R^3$, $R^4$, $R^5$, $R^6$, $R^7$, and $R^8$ independently represent a hydrogen atom, an alkyl group or an alkoxy group having 1 to 5 carbon atoms that may be branched, a hydroxyl group or a halogen atom or a nitro group or an amino group that may be substituted, and wherein any one of $R^1$ to $R^8$ is the linker part L.

3. The electron mediator according to claim 2, wherein the electron mediator is that represented by any one of Formula (I-1) to (I-16):

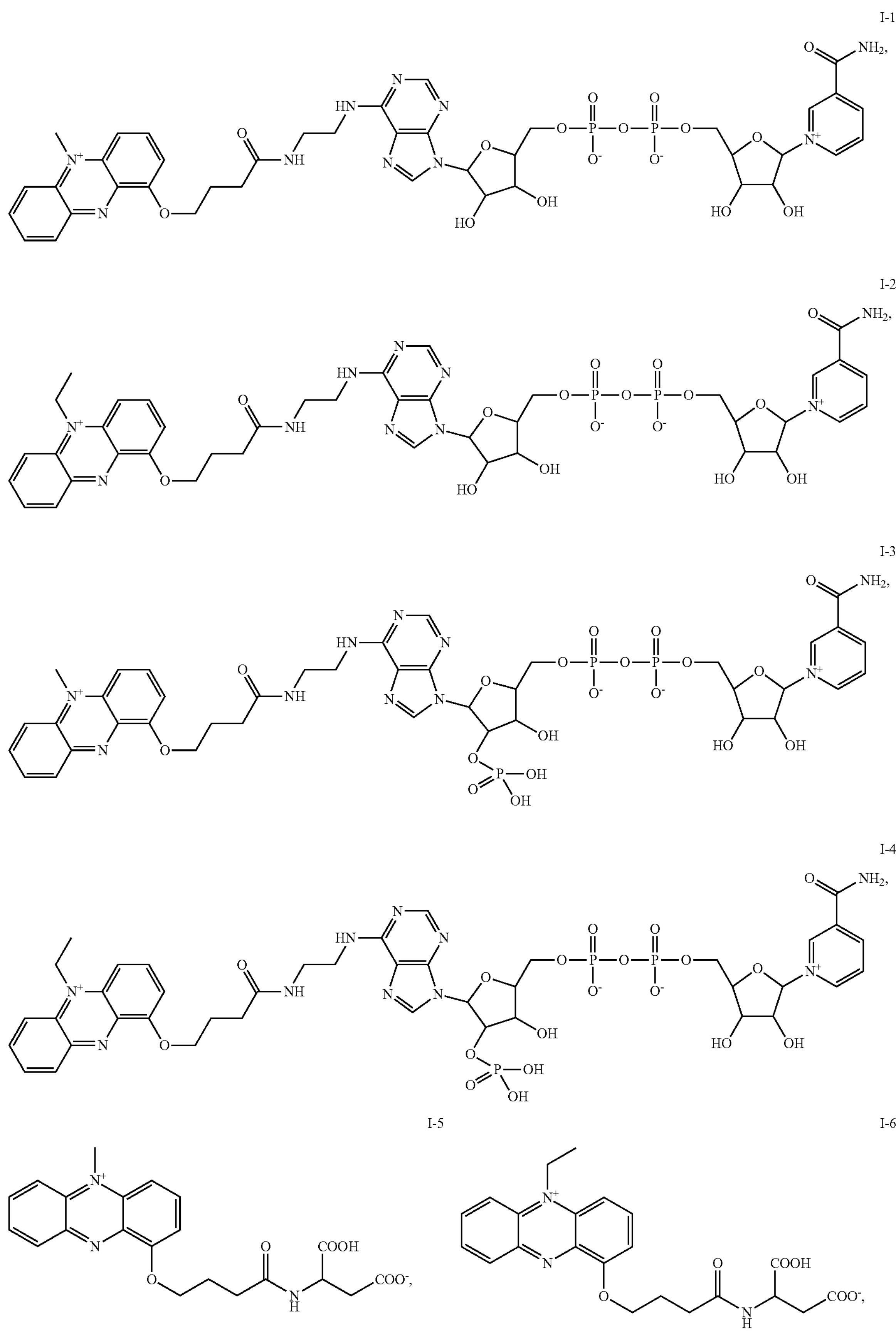
I-1
I-2
I-3
I-4
I-5
I-6

-continued

I-7

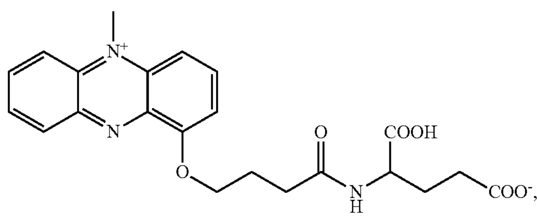

I-8

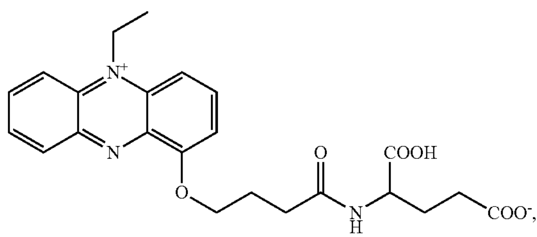

I-9

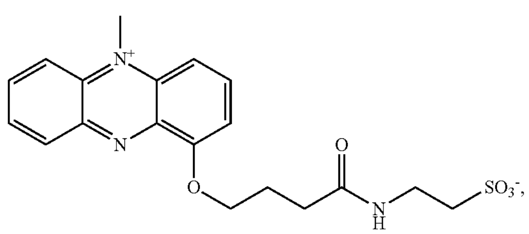

I-10

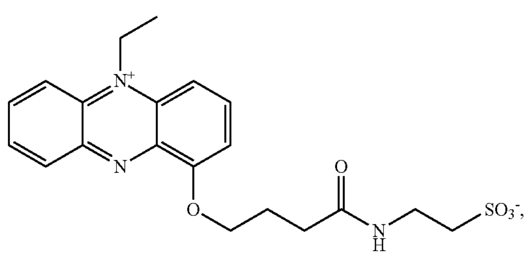

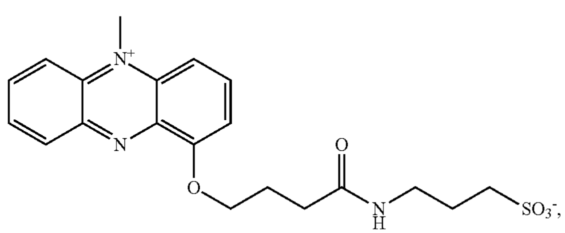

I-12

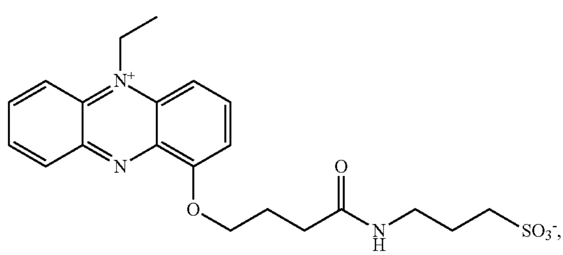

I-13

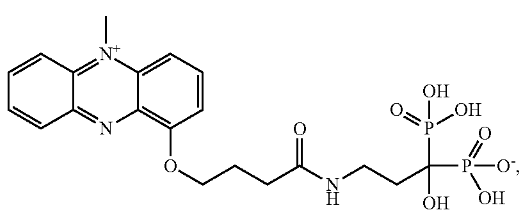

I-14

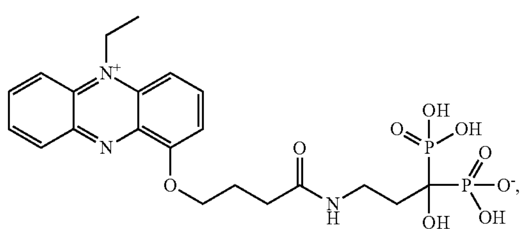

I-15

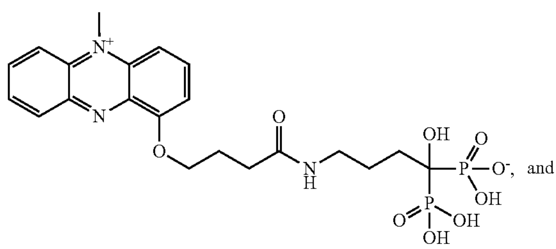

I-16

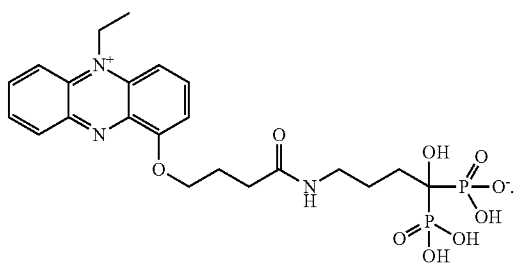

4. A measurement reagent for dehydrogenase and substrate thereof comprising the electron mediator according to claim 2.

5. The measurement reagent according to claim 4, wherein the dehydrogenase is lactate dehydrogenase and the measurement reagent includes a substrate for lactate dehydrogenase.

6. The measurement reagent according to claim 4 further comprising a co-enzyme.

7. The measurement reagent according to claim 4 further comprising a reductive chromogenic dye.

8. The measurement method according to claim 1, wherein the electron mediator is that represented by any one of Formula (I-1) to (I-16):

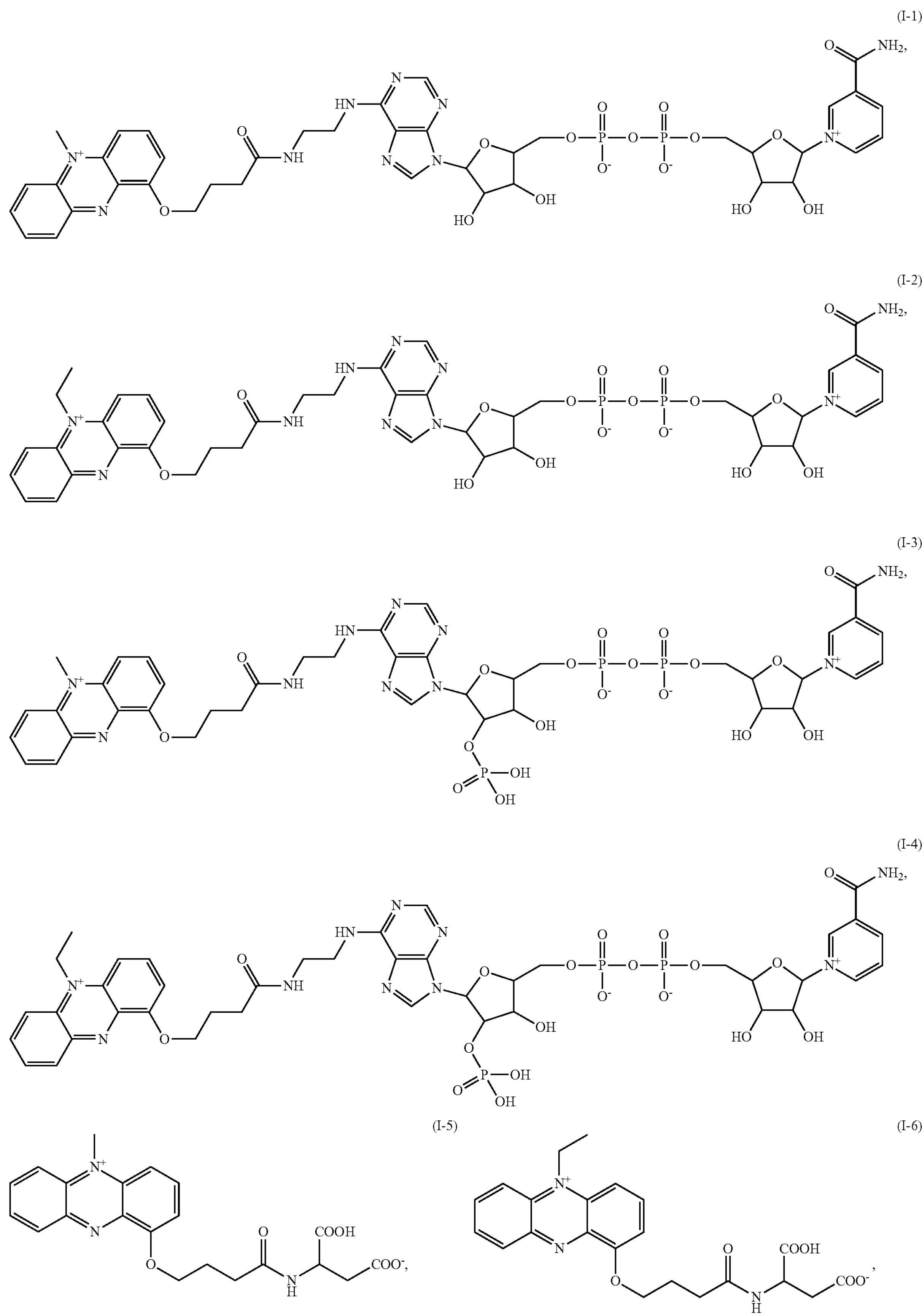
(I-1)
(I-2)
(I-3)
(I-4)
(I-5)
(I-6)

-continued (I-7)

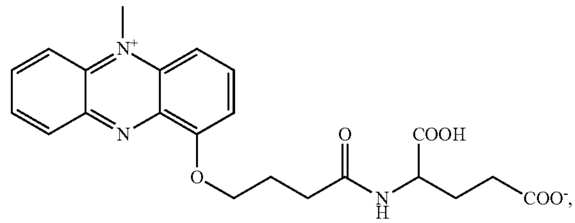

(I-8)

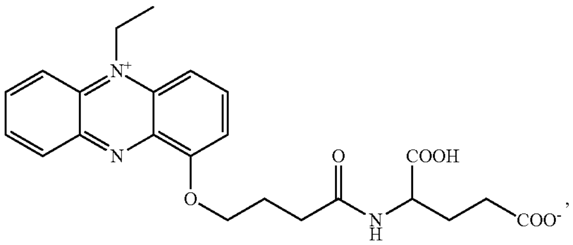

(I-9)

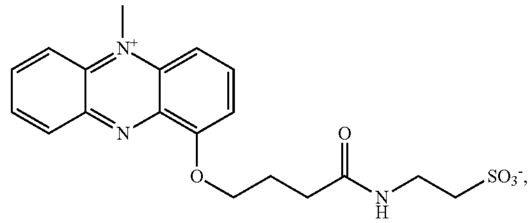

(I-10)

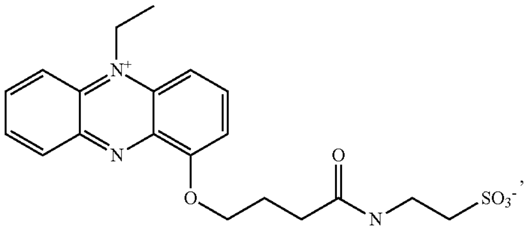

(I-11)

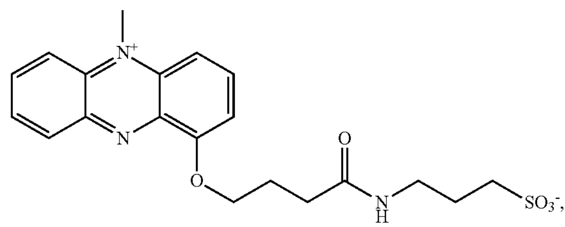

(I-12)

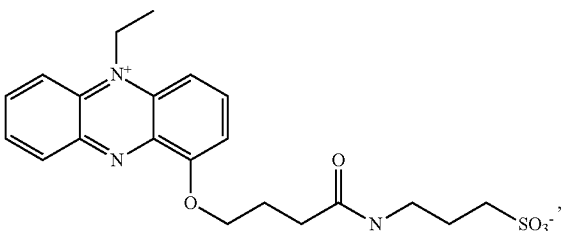

(I-13)

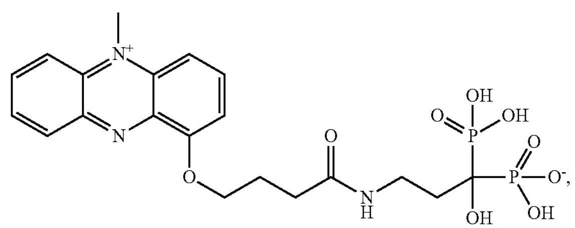

(I-14)

(I-15)

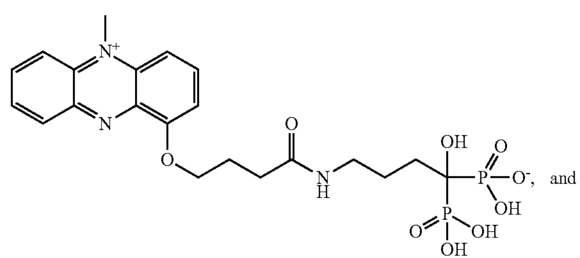

(I-16)

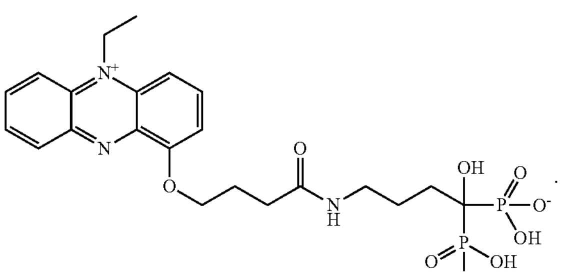

9. The measurement method according to claim 1, wherein the linker part L for linking the structural part A containing the at least one anionic group and the structural part M for mediating electron transfer is $R^4$, and wherein $R^4$ is an alkoxy group.

10. The electron mediator of claim 2, wherein X represents an alkyl group.

11. The electron mediator of claim 2, wherein A is an amino acid selected from aspartic acid and glutamic acid.

12. The electron mediator of claim 2, wherein A is an amino sulfonic acid selected from taurine and homotaurine.

13. The electron mediator of claim 2, wherein A is an amino phosphoric acid selected from pamidronic acid and alendronic acid.

14. The electron mediator of claim 2, wherein A is a nucleotide selected from nicotine amide dinucleotide and nicotine amide dinucleotide phosphate.

15. The measurement method according to claim 8, wherein the electron mediator is that represented by any one of Formula (I-5) to (I-8).

16. A measurement method for concentration of a dehydrogenase and substrate thereof in the presence of living cells, comprising adding a chromogenic solution to a cell sample containing the dehydrogenase and living cells, the chromogenic solution comprising the electron mediator of claim 2, a co-enzyme and a reductive chromogenic dye and detecting a color change resulting from reduction of the chromogenic dye.

* * * * *